US008560281B2

(12) United States Patent
Soto et al.

(10) Patent No.: US 8,560,281 B2
(45) Date of Patent: *Oct. 15, 2013

(54) METHODS AND SYSTEMS FOR UTILIZING PREDICTION MODELS IN HEALTHCARE

(75) Inventors: Gabriel Enrique Soto, Chesterfield, MO (US); John Albert Spertus, Kansas City, MO (US)

(73) Assignee: Health Outcomes Sciences, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/615,401

(22) Filed: Sep. 13, 2012

(65) Prior Publication Data
US 2013/0006662 A1     Jan. 3, 2013

Related U.S. Application Data

(63) Continuation of application No. 12/620,985, filed on Nov. 18, 2009, now Pat. No. 8,285,525, which is a continuation of application No. 11/072,209, filed on Mar. 4, 2005, now Pat. No. 7,643,969.

(51) Int. Cl.
*G06F 7/60* (2006.01)
*G06F 17/10* (2006.01)

(52) U.S. Cl.
USPC .......................................................... 703/2

(58) Field of Classification Search
USPC .......................................................... 703/2
See application file for complete search history.

(56) References Cited

U.S. PATENT DOCUMENTS

| | | | |
|---|---|---|---|
| 4,839,822 A | 6/1989 | Dormond et al. | |
| 4,846,190 A | 7/1989 | John | |
| 5,517,405 A | 5/1996 | McAndrew et al. | |
| 5,860,917 A | 1/1999 | Comanor et al. | |
| 6,120,460 A | 9/2000 | Abreu | |
| 6,333,160 B1 | 12/2001 | Tamura | |
| 6,368,272 B1 * | 4/2002 | Porumbescu | 600/300 |
| 6,385,589 B1 | 5/2002 | Trusheim et al. | |
| 7,081,347 B2 | 7/2006 | Yusuf et al. | |
| 7,134,994 B2 | 11/2006 | Alpert et al. | |
| 7,187,992 B2 | 3/2007 | Tuszynski | |
| 7,643,969 B2 | 1/2010 | Soto et al. | |
| 8,285,525 B2 * | 10/2012 | Soto et al. | 703/2 |
| 2002/0165855 A1 | 11/2002 | Ohtomo | |

(Continued)

FOREIGN PATENT DOCUMENTS

WO     WO 03/104939     12/2003

OTHER PUBLICATIONS

"Virtual Offices Basic Manual for Professionals" by Help Horizons.com v.1.14, Apr. 2001, 60 pages.

(Continued)

*Primary Examiner* — Dwin M Craig
(74) *Attorney, Agent, or Firm* — Knobbe, Martens, Olson & Bear LLP

(57) ABSTRACT

A method for providing decision support includes using a programmed computer to input a regression model specification, and to repeat the input a plurality of times to obtain and store a plurality of regression model specifications. The method further includes using the programmed computer to analyze selected regression model specifications to determine at least one of common variables and functions of common variables, to thereby determine a reduced-redundancy request for input of variables, when a plurality of the stored regression model specifications are selected for use.

32 Claims, 13 Drawing Sheets

(56) References Cited

U.S. PATENT DOCUMENTS

2003/0229513 A1 12/2003 Spertus
2004/0103073 A1 5/2004 Blake et al.
2004/0172291 A1 9/2004 Knowlton

OTHER PUBLICATIONS

An International Search Report, dated Sep. 11, 2007, for International Application No. PCT/US06/07849.
Charles Hu, et al.; http://www.medcacl.comlheartrisk.html; Coronary Heart Disease Risk Calculator; Jan. 15, 2000; 1 sheet.
Coleen A. McHorney, et al., "The MOS 36-Item Short-Form Health Survey (SF-36): II. Psychometric and Clinical Tests of Validity in Measuring Physical and Mental Health Constructs", *Medical Care*, 1993, pp. 247-263, vol. 31—No. 3, J.B. Lippincott Company.
Elizabeth R. Delong, et al., "Comparing the Areas Under Two or More Correlated Receiver Operating Characteristic Curves: A Nonparametric Approach," *Biometrics*, Sep. 1988; pp. 837-845, vol. 44.
Eric L. Eisenstein, et al., "Assessing the Clinical and Economic Burden of Coronary Artery Disease: 1986-1998," *Medical Care*; Nov. 8, 2001; pp. 824-835; vol. 39—No. 8; Lippincott Williams & Wilkins. Inc.
Frederic D. Wolinsky, et al., "Perceived Health Status and Morality Among Older Men and Women," *Journal of Gerontology*, 1992, pp. S304-S312, vol. 47—No. 6.
Ga L'Abbate, et al., "On-Line Integration and Analysis of Cardiological Data to Support Medical Decision Making", *IEEE, Computers in Cardiology*, 2004, pp. 189-192, vol. 31.
Gabriel E. Soto, et al., "PRISM Update: Experiences Using a Web-based Framework for the Deployment of Predictive Clinical Models at the Point of Care," *Poster Presentations e341*, Circulation (Supplement), vol. 111, p. e341, 2005.
Gabriel E. Soto, et al., "PRISM: A Novel Tool for Deploying Predictive Clinical Models; Circulation," May 25, 2004; p. 47; vol. 109—No. 20.
G.E. Soto, et al, "PRISM™: A Web-Based Framework for Deploying Predictive Clinical Models," *Computers in Cardiology*; Nov. 2004; pp. 193-196; vol. 31; *IEEE*.
John Spertus, et al., "Association Between Depression and Worse Disease-Specific Functional Status in Outpatient with Coronary Artery Disease," *American Heart Journal*; Jul. 2000; pp. 105-11 0; vol. 1 40—No. 1.
John Spertus, et al., "Health Status Predicts Long-Term Outcome in Outpatients with Coronary Disease", *Circulation—Journal of the American Heart Association*, Jul. 2, 2002, pp. 43-49.
John A. Spertus, et al., "Development and Evaluation of the Seattle Angina Questionnaire: A New Functional Status Measure for Coronary Artery Disease," *JACC*; Feb. 1995; pp. 333-341; vol. 25No. 2; American College of Cardiology.
John A. Spertus, et al., "Monitoring the Quality of Life in Patients with Coronary Artery Disease," *The American Journal of Cardiology*; Dec. 15, 1994; 1240-1244; vol. 74.
John S. Rumsfeld, et al., "Health-Related Quality of Life as a Predictor of Mortality Following Coronary Artery Bypass Graft Surgery," *JAMA*; Apr. 14, 1999; pp. 1298-1 303; vol. 281—No. 14.
Peter C. Block et al., "Identification of Variables Needed to Risk Adjust Outcomes of Coronary Interventions: Evidence-Based Guidelines for Efficient Data Collection," *JACC*; Jul. 1998, pp. 275-282, vol. 32—No. 1: Elsevier Science Inc.
Philip S. Wells, et al., "Accuracy of Clinical Assessment of Deep-Vein Thrombosis," *The Lancet*, May 27, 1995 ; pp. 1326-1330, vol. 345.
Rabin, D. S.; Qadeer; U.; Steir, V.E. "A Cost and Outcome Model of Fertility Treatment in a Managed Care Environment," *Fertility & Sterility* 1996, 66, 896-903.
Robert H. Jones, et al., "Identification of Preoperative Variables Needed for Risk Adjustment of ShortTerm Mortality after Coronary Artery Bypass Graft Surgery," JACC; Nov. 15, 1996; pp. 1478-1487; vol. 28—No. 6; Elsevier Science Inc.
Robert M. Califf, et al., "Importance of Clinical Measures of Ischemia on the Prognosis of Patients with Documents Coronary Artery Disease," *JACC*; Jan. 1988; pp. 20-26; vol. 11—No. I; Elsevier Science Inc.
Salim Yusuf, et al., "Effect of Coronary Artery Bypass Graft Surgery on Survival: Overview of 10-year result from Randomised Trials by the Coronary Artery Bypass Graft Surgery Trialists Collaboration," *The Lancet*, Aug. 27, 1997, pp. 563-570, vol. 344.
Susan Gross Fisher, et al., "Mortality Ascertainment in the Veteran Population: Alternatives to the National Death Index," *American Journal of Epidemiology*, 1995; vol. 141—No. 3; The Johns Hopkins University School of Hygiene and Public Health.
T A Rockall, et al., "Risk Assessment After Acute Upper Gastrointestinal Hemorrhage," *Gut*, 1996, pp. 316-321, vol. 38.
Visiontree; various pages from http:/www.idegomethodologies.com; 2004; Idego Methodologies; 19 sheets.
William A. Knaus, et al., "Apache II: A Severity of Diseases Classification System" *Critical Care Medicine*, Oct. 1985, pp. 818-829, vol. 13—No. 10; The Williams & Witkins Co.
William Cassidy; http://archive.gamespy.wmlhalloffame/septemberO2/pcs/; Pinball Construction Set; Bill Budge and Electronic Arts; 4 sheets, 1983.

* cited by examiner

Model Details
_____

General Information:
_____

Name: | Angina Symptoms at One Year (Angioplasty/Stent) |

Outcome: | Probability of Having Angina Symptoms at One Year ▼|

Description: | This model predicts the probability of having angina symptoms at one year for patients undergoing a percutaneous intervention for their coronary artery disease. Data for the model is derived from 1199 subjects participating in INFORM, a registry of Acute Coronary Syndrome (ACS) patients at the Mid America Heart Institute and Truman Medical Center (Kansas City, MO). |

Model Type: | Generalized Linear ▼ |

Version: | 1.0.0 |

Build Status: In Progress

Active: ☑

Publish: ☑

Fig. 4A

Model Structure:

Link Function: [Logit ▼]          Linear Predictor $\eta$:

Inference: [Population ▼]         $\eta = \beta_0 + \beta_1 x_{\tau\text{-}1} + \ldots + \beta_\eta x_{\tau\text{-}\eta}$ Intercept Term(s): [✓]            Where coefficients $\beta_0, \ldots, \beta_\eta$
                                  and terms $x_{\tau\text{-}1}, \ldots, x_{\tau\text{-}\eta}$
Error Parameterization: [✓]       are defined below. Estimator $\mu$:

$$\mu = (1+e^{-\eta})^{-1}$$

Output Plot Options:

Plot Label: [Angioplasty]

Condensed Plot Label: [PCI]       *(For mobile devices)*

Model Parameters: ($X_1, X_2, \ldots, X_N$)                    [Edit List]

| Name | Category | Type |
| --- | --- | --- |
| Age | Demographics | Continuous |
| Angina | Patient Characteristics | Nominal |
| AvoidCare | Patient Characteristics | Nominal |
| LungDisease | Comorbidities | Binary |
| SF12PCS | Clinical Characteristics | Continuous |

Parameter Transformations: ($X_K \rightarrow X_{T\text{-}1}, X_{T\text{-}2}, \ldots$)    [Add New Transformation]

| Name | Parameter | Type | |
| --- | --- | --- | --- |
| Age | Age | Identity | [Edit] |
| Ang_IndR2 | Angina | Indicator | [Edit] |
| AvCr_IndR2 | AvoidCare | Indicator | [Edit] |
| LungDz | LungDisease | Identity | [Edit] |
| SF12PCS | SF12PCS | Identity | [Edit] |

Model Terms: ($X_{T\text{-}1}, X_{T\text{-}2}, \ldots, X_{T\text{-}N}$)              [Add New Term(s)]

Fig. 4B

| Name | Description | Degenerate | | |
|------|-------------|------------|---|---|
| Angin_i1 | 1 if Angina r=1; 0 otherwise | ☑ | ↑↓ | [Edit] |
| Angin_i2 | 1 if Angina r=2; 0 otherwise | ☑ | ↑↓ | [Edit] |
| Avoid_i1 | 1 if AvoidCare r=1; 0 otherwise | ☑ | ↑↓ | [Edit] |
| Avoid_i2 | 1 if AvoidCare r=2; 0 otherwise | ☑ | ↑↓ | [Edit] |
| Age_ID | Age | ☑ | ↑↓ | [Edit] |
| LungD_ID | LungDisease[0/1] | ☑ | ↑↓ | [Edit] |
| SF12P_ID | SF12PCS | ☑ | ↑↓ | [Edit] |

Coefficient Vector: $(\beta_0, \beta_1, ..., \beta_\eta)$  ▶ Import

| Intercept ($\beta_0$) | Angin_i1 ($\beta_1$) | Avoid_i1 ($\beta_2$) |
|---|---|---|
| 0.5946918691 | 0.4675835737 | 0.87075678 |

| Age_ID ($\beta_3$) | LungD_ID ($\beta_4$) | SF12P_ID ($\beta_5$) |
|---|---|---|
| -0.020630729 | 1.0356287352 | -0.026204752 |

Error Parameterization: *(Required for computing confidence intervals)*

Covariance Matrix:  ▶ Import

| | Intercept ($c_0$) | Angin_i1 ($c_1$) | Avoid_i1 ($c_2$) | Age_ID ($c_3$) | LungD_ID ($c_4$) |
|---|---|---|---|---|---|
| Intercept ($c_0$) | 0.456042215 | -0.117099971 | -0.042157233 | -0.003534012 | -0.0187443 |
| Angin_i1 ($c_1$) | -0.117099971 | 0.1138507627 | 0.0072959287 | -0.000009428 | 0.00306582 |
| Avoid_i1 ($c_2$) | -0.042157233 | 0.0072959287 | 0.048365083 | 0.0003534514 | 0.00014297 |
| Age_ID ($c_3$) | -0.003534012 | -0.000009428331 | 0.0003534514 | 0.0000506005 | -0.0000140 |
| LungD_ID ($c_4$) | -0.018744335 | 0.0030658202 | 0.0001429759 | -0.000014042 | 0.06492194 |
| SF12P_ID ($c_5$) | -0.002432639 | 0.0001835103 | 0.0001659837 | 0.000007332421 | 0.00025297 |

NOTE: Values below the diagonal will be refreshed on 'Update'

Update    Delete this model    Cancel

Fig. 4C

Edit Outcome Definition

General Information:

- Name: New Outcome
- Outcome: One Year Outcomes (INFORM) ▼
- Description: Test outcome
- Type: Survival ▼
- Active Status: ☐

Output Plot Options:

Output Styles:

- Solid Bar
- Digital
  - Op1: 06 (75,85)
  - Op2: 61 (57,64)
  - Op3: 50 (40,53)

- Caption: Test
- Subtitle:
- Minimum Value: 0
- Maximum Value: 1
- Scale Factor: 1
- Use Custom Axis Labels: ☐
- Use Scale Annotations: ☐

Custom Reports: [Add New Report]

| Report Name | |
|---|---|
| Test report | [Edit] |

Update    Delete this outcome    Cancel

Fig. 5

Edit Parameter Definition
───────────────────────────────────────────────

General Information:
───────────────────────────────────────────────

Name: | Angina |

Category: | Patient Characteristics ▼ |

Description: | Assessment of Angina Frequency. This question is derived from the Seattle Angina Questionnaire (Item number 4). |

Type: | Nominal ▼ |

Active Status: ■

Rendering/Collection Details:
───────────────────────────────────────────────

Full Text: | Over the past four weeks, have you had any chest pain, chest tightness or angina, or taken nitroglycerin (tablets or spray) for these symptoms? |

Short Text: | Angina within 4 weeks |

───────────────────────────────────────────────

Responses:

| | Item | Full Text | Condensed | [Add Response] |
|---|---|---|---|---|
| ✎ ✗ | 1 | Yes | Y | |
| ✎ ✗ | 2 | No | N | |

Report Name                                      [Edit]
Test report

───────────────────────────────────────────────

Update    Delete this outcome    Cancel
───────────────────────────────────────────────

Fig. 6

Home ClinicalTools Workgroup Discussions About ManageLibraries ManagePortal
Manage Account | Logoff Outcome Models No patient selected.                                    Select Patient Category: [All ▼]                                       Select All: ☑

---

☑ ⊞ Angina Symptoms at One Year (Angioplasty/Stent)

☑ ⊞ Angina Symptoms at One Year (Bypass Surgery)

☑ ⊞ Angina Symptoms at One Year (Medical Management)

☑ ⊞ In-Hospital Mortality for AMI in NSTEMI Patients

☑ ⊞ In-Hospital Mortality for AMI in STEMI Patients

---

Page 1 of 4
[ << Previous Page] [Next Page >>]          View: 5 | 10 | 15 | 20 | 25

---

To run one or more of the above models, simply follow these three steps:

● Click 'Select Patient' to use an existing record or to add a new patient.

● Place a check by the model(s) you wish to run.

⦿ Click to 'Run Selected Model(s)'.

Fig. 8

Please complete all of the requested items below:

1. Age (years): `55`
2. Gender:
   - ◉ Male
   - ○ Female
3. History of Diabetes: ☑
4. History of Renal Failure: ☐
5. History of Recent Heart Failure: ☐
6. History of Prior PCI: ☐
7. History of Chronic Lung Disease: ☑
8. History of Cerebrovascular Disease: ☐
9. History of Peripheral Vascular Disease: ☐
10. LV Ejection Fraction: `0.7`
11. NYHA Class II - IV: ☐
12. Non-elective PCI: ☐
13. Shock at the Time of PCI: ☑
14. Left Main Coronary Artery Lesion: ☐
15. Proximal LAD Coronary Artery Lesion: ☐
16. AHA Lesion Type:
    - ○ Low Risk (Type A)
    - ◉ Moderate Risk (Type B)
    - ○ High Risk (Type C)
17. Graft Treated: ☑

Fig. 9

METHODS AND SYSTEMS FOR UTILIZING PREDICTION MODELS IN HEALTHCARE

BACKGROUND OF THE INVENTION

This invention relates generally to methods and apparatus for providing statistical estimates useful for decision support, including computer networks and software configured to provide such decision support. The methods and apparatus described herein are particularly useful for providing information to health care providers and medical patients, but are not limited to such environments and can be used in a wide variety of fields in which regression analysis or statistical modeling is used as a decision support tool.

This application hereby incorporates by reference in its entirety another application filed on even date by the same inventors as PCT/US06/07849 and entitled "System and Methods for Risk Stratification of Patent Populations."

The past decade of health services research has witnessed an explosion of prognostic models to help physicians understand the risks and benefits of proposed medical therapies. However, the application of such models to clinical practice has been limited by both their complexity and the lack of a practical mechanism for making them available at the time of medical decision-making.

The emergence of the internet and mobile computing devices has created new opportunities for researchers in the health care field to translate their evidence-based predictive models into clinical decision aids. However, a number of barriers continue to prevent researchers from taking advantage of these technologies, including: (1) a requisite expertise in a computer programming language or application development environment; (2) the challenge of creating a system that can adapt to a broad range of clinical practice settings, each with unique device and work-flow constraints; (3) the need for a sustainable mechanism for updating predictive models and deploying revisions in a timely fashion; and (4) the difficulty of integrating with existing IT infrastructures and disparate clinical information systems.

Furthermore, both the patient and the attending health care professional should be involved in making clinical health care treatment decisions that affect the patient's desired heath goals and quality of life concerns. These decisions may vary depending upon the patient's age, sex, socioeconomic, demographic, clinical, and genetic or imaging characteristics, which generally affect the relative risk and benefits of outcomes of medical and surgical procedures.

BRIEF DESCRIPTION OF THE INVENTION

In one aspect, the present invention provides a machine-readable medium or media having instructions recorded thereon that are configured to instruct a processor to input a regression model specification, and to repeat this input a plurality of times to obtain and store a plurality of regression model specifications. The instructions also are configured to analyze selected regression model specifications to determine at least one of common variables and functions of common variables, to thereby determine a reduced-redundancy request for input of variables, when a plurality of the stored regression model specifications are selected for use.

In another aspect, the present invention provides a method for providing decision support. The method includes using a programmed computer to input a regression model specification, and to repeat the input a plurality of times to obtain and store a plurality of regression model specifications. The method further includes using the programmed computer to analyze selected regression model specifications to determine at least one of common variables and functions of common variables, to thereby determine a reduced-redundancy request for input of variables, when a plurality of the stored regression model specifications are selected for use.

In yet another aspect, the present invention provides a computer network that includes a server computer and a server module. The server computer includes a processor and a memory. The computer network also includes a first client computer, not necessarily different from the server computer. The first client computer includes a first user display device, a first user input device, and a client module. The computer network also includes a second client computer, not necessarily different from the first client computer or the server computer. The second client computer has a second user display device not necessarily different from the first user display device, a second user input device not necessarily different from the first user input device, and a second client module. The server module includes instruction code configured to (a) instruct the processor to communicate common regression models to the first client module and store a regression model specification received from the first client module, (b) to repeat (a) a plurality of times to obtain and store a plurality of the regression model specifications; and, (c) when a plurality of the stored regression model specifications are selected for use, to analyze the selected regression model specifications to determine at least one of common variables and functions of common variables, to thereby determine a reduced-redundancy request for input of variables.

It will thus be appreciated that configurations of the present invention facilitate rapid translation of evidenced-based predictive models into robust tools (for example, web-based tools) capable of providing visual representations of predicted outcomes. When used in a medical environment to provide outcome predictions at the point of patient care; configurations of the present invention can be used to rapidly disseminate the newest knowledge to the clinical setting.

Moreover, outcomes researchers can use configurations of the present invention to create powerful evidence-based tools that deliver decision support at the point of care for diagnostic workups and treatment selection. In the management of acute coronary syndromes (ACS), for example, physicians can get immediate probability estimates for outcomes such as survival, angina frequency, or physical limitation at one year for all possible treatment options, as well as risk-projections for procedural complications.

Some configurations provide a broad assortment of graphical output options that facilitate the sharing of information with patients, thereby allowing physicians and patients to reach a consensus decision regarding therapy that best meets the desires, needs, and expectations of the patient. Some configurations can be or are useful for producing "informed consent" documents and/or documentation of discussion of procedural risks and benefits with patients, and/or for other uses.

BRIEF DESCRIPTION OF THE DRAWINGS

FIG. 4 is an example of a display of a visual selection of parametric regression model forms.

FIG. 5 is an example of a display of an outcome type screen.

FIG. 6 is an example of a display of a parameter name screen.

FIG. 8 is an example of a display that provides a visual selection of previously stored models.

FIG. 9 is an example of a display requesting parameter data.

DETAILED DESCRIPTION OF THE INVENTION

Figure 1:
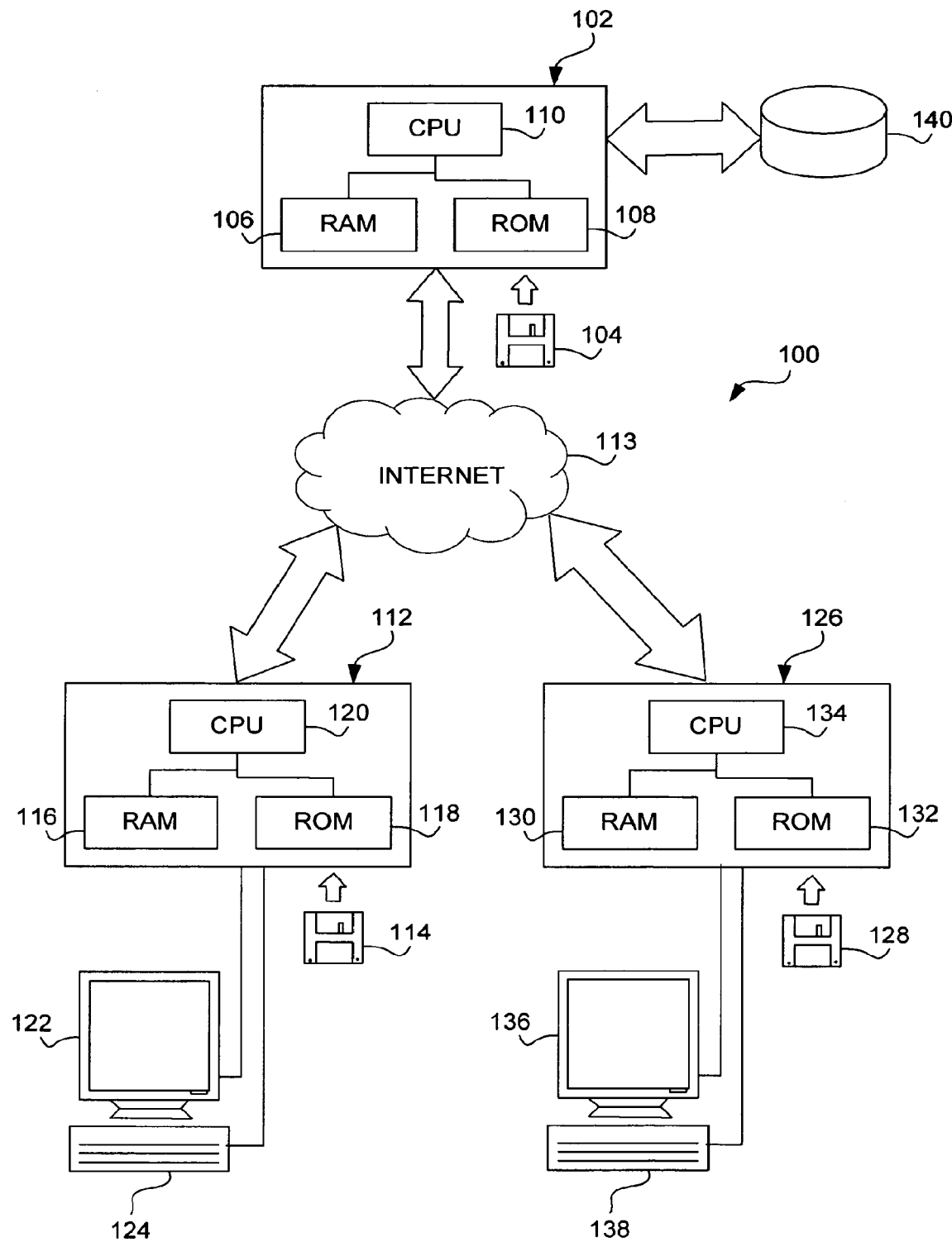
FIG. 1 is a pictorial block diagram of a configuration of a computer network of the present invention.

Technical effects of configurations of the present invention include the generation of visual displays and printed reports useful for decision making in various fields. Thus, In some configurations of the present invention and referring to FIG. 1, a computer network 100 is configured for providing decision support. Decision support computer network 100 may be used, for example, in a medical or clinical health care environment to identify an appropriate regimen for treatment of a medical condition. However, uses for computer network 100 are not limited to the health field. To give but one of many examples, decision support computer network 100 is useful in an advertising environment to determine strategies for marketing products. More generally, computer network 100 is useful in many varied contexts in which statistical regression models can be used to predict outcomes. To provide decision support, some configurations of the present invention are configured to generate outputs, including graphical outputs and patient reports that incorporate such outputs.

In some configurations, computer network 100 comprises a server computer 102 that executes a server module. The server module comprises software instructions recorded on a machine-readable medium or media 104. The machine readable medium or media may comprise, for example, one or more floppy diskettes, CD-ROMs, CD-RWs, DVDs, DVD+Rs, DVD-Rs, DVD+RWs, DVD-RWs, memory devices such as USB memory sticks or other types of memory cards, internal readable and writable memory 106 of any of various kinds, such as internal or external RAM, etc., read-only memory (ROM) 108 of any of various kinds, hard disks, optical drives, and combinations thereof. (As used herein, "media" includes not only "removable" media, but also "non-removable" media such as primary and secondary storage. For example, RAM, ROM, and hard disk drives are included as "media," as well as the aforementioned types of media.) Server computer 102 can include devices (not specifically illustrated in FIG. 1) for reading removable media, such as a CD-ROM drive, a DVD drive, a floppy disk drive, etc. In many configurations, server computer 102 will comprise at least a readable and writeable memory 106, read-only memory 108 or non-volatile memory of a suitable type, and a processor 110 (e.g., a central processing unit or CPU) which may itself comprise one or more microprocessors, coprocessors, etc. Thus, the term "processor," as used herein, is not literally restricted to a single CPU. Moreover, server computer 102 may itself comprise a network of one or more computers, as can any other device referred to as a "computer" herein.

Computer network 100 further comprises one or more first client computers 112. In many configurations, it is in communication with server computer 102 via a network 113, for example, the Internet. In many configurations of the present invention, Client computer 112 comprises a first client module comprising software instructions recorded on a machine-readable medium or media 114. In many configurations, client computer 112 further comprises at least a readable and writable memory 116, read-only memory 118, and a processor 120 that may itself comprise one or more microprocessors, coprocessors, etc. First client computer 112 may itself comprise one or more computers in a network. First client computer 112 further comprises a first user display device 122, such as a CRT display, LCD display, plasma display, and/or a hardcopy device such as a printer. First client computer 112 also comprises a first user input device 124, such as a keyboard, a mouse, a touch screen (which may be part of display 122), and/or a trackball, etc. First client computer 112 is not limited to desktop and laptop computers but can include any computing device that can communicate over a network. For example, in some configurations, a first client computer 112 can be a personal digital assistant (PDA) or a wireless telephone with a display screen.

Computer network 100 further comprises one or more second client computers 126. In many configurations, second client computer 126 is in communication with server computer 102 via network 113. Also in many configurations, second client computer 126 comprises a second client module comprising software instructions recorded on a machine-readable medium or media 128. In many configurations, second client computer 126 further comprises at least a readable and writable memory 130, read-only memory 132, and a processor 134 that may itself comprise one or more microprocessors, coprocessors, etc. Second client computer 126 may itself comprise one or more computers in a network. Second client computer 126 further comprises a second user display device 136, such as a CRT display, LCD display, plasma display, and./or a hardcopy device such as a printer. Second client computer 126 also comprises a second user input device 138, such as a keyboard, a mouse, a touch screen (which may be part of display 136), and/or a trackball, etc.

As used herein, software instructions are said to "instruct a computer to display" information even if such information is communicated via a network to another computer for display on a remote display terminal. In this sense code running on a web server instructs a processor executing that code to "display" a web page, even though the code actually instructs the processor to communicate data via a network that allows a browser program to instruct another computer to construct a display of the web page on the display of the other computer. For example, the server module described in the examples presented herein can include a web server and the client modules can comprise web browsers. Also, in some configurations, client computers 112 and 126 comprise laptop, desktop, or mobile computing devices or communication terminals. The broader scope of the phrase "instruct a computer to display" is used because server computer 102 and the one or more client computers 112, 126 need not necessarily be different computers. For example, communication protocols known in the art allow a server software module and a client software module running on a multitasking computer system to communicate with one another on the same computer system, and the same server software module can also communicate with a client software module running on a different computer via a network connection. The examples used herein assume, without loss of generality, that different physical computers and a network are used, as such will be the case in many, but not all, configurations of the present invention.

The terms "display" and "accept" as used in the descriptions herein refer to a suitably programmed computing apparatus "displaying" or "accepting" data, not to a person "displaying" or "accepting" something. A person might, however, view the displayed data on an output device or on a page produced by an output device or supply the accepted data using an input device.

In some configurations of the present invention, a method is provided to provide decision support via software that comprises the server module. Some configurations of the present invention provide server modules that utilize the ASP-.NET platform available from Microsoft Corporation, Redmond, Wash. as well as MS Internet Information Services (IIS) and MS SQL Server from Microsoft Corporation for web services and data storage, respectively. A multi-tier system architecture provided in some configurations enables scaling of server module components as needed to meet specific demands of a particular deployment. In addition, a modular design framework is provided in some configurations to facilitate extensibility and incorporation of new functionality via custom modules. In some configurations, the server module is written in C# using the code-behind convention; except for its SQL data access components which are stored procedures written in Transact-SQL. Configurations of the present invention are not limited to implementation using the tools described above. For example, configurations of the present invention can run on the LINUX® operating system (LINUX is a trademark of Linus Torvalds) and be built using a different suite of applications. The selection of an appropriate operating system and suite of applications can be left as a design choice to one of ordinary skill in the art after such a person gains an understanding of the present invention from the present description.

Figure 2A:
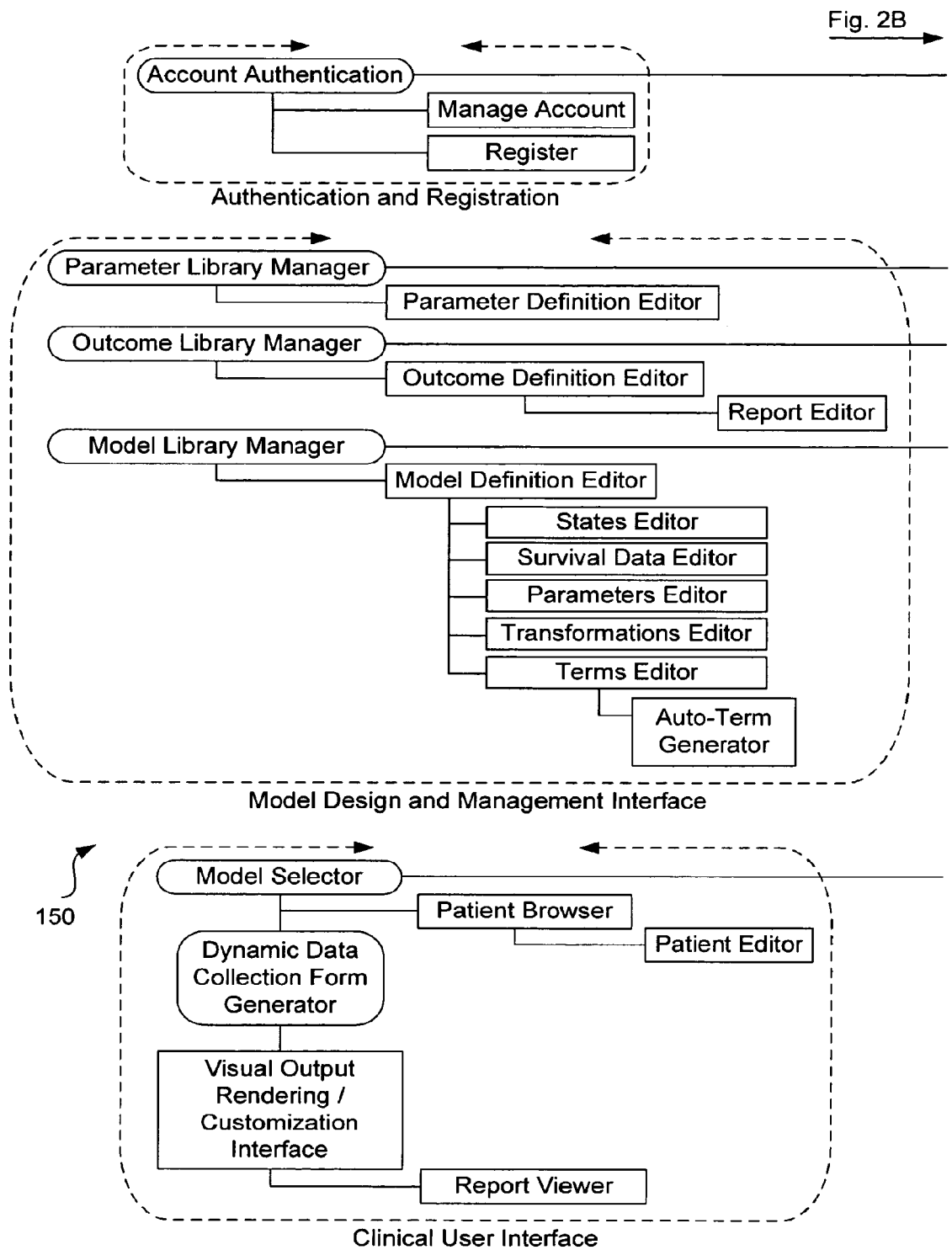
FIG. 2 is a block diagram showing the logical structure of an example configuration of a server module.
Figure 2B:
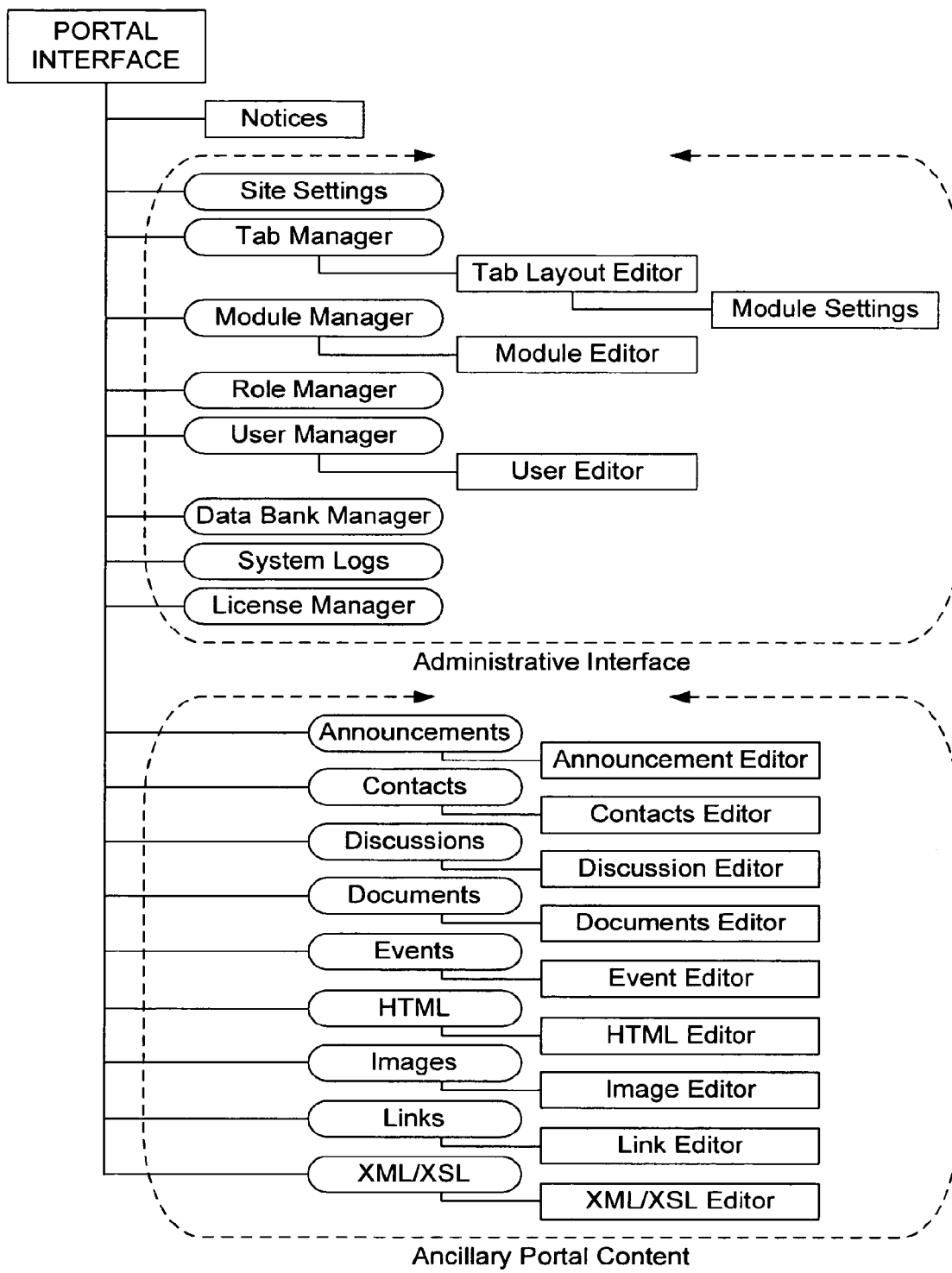
Figure 3:
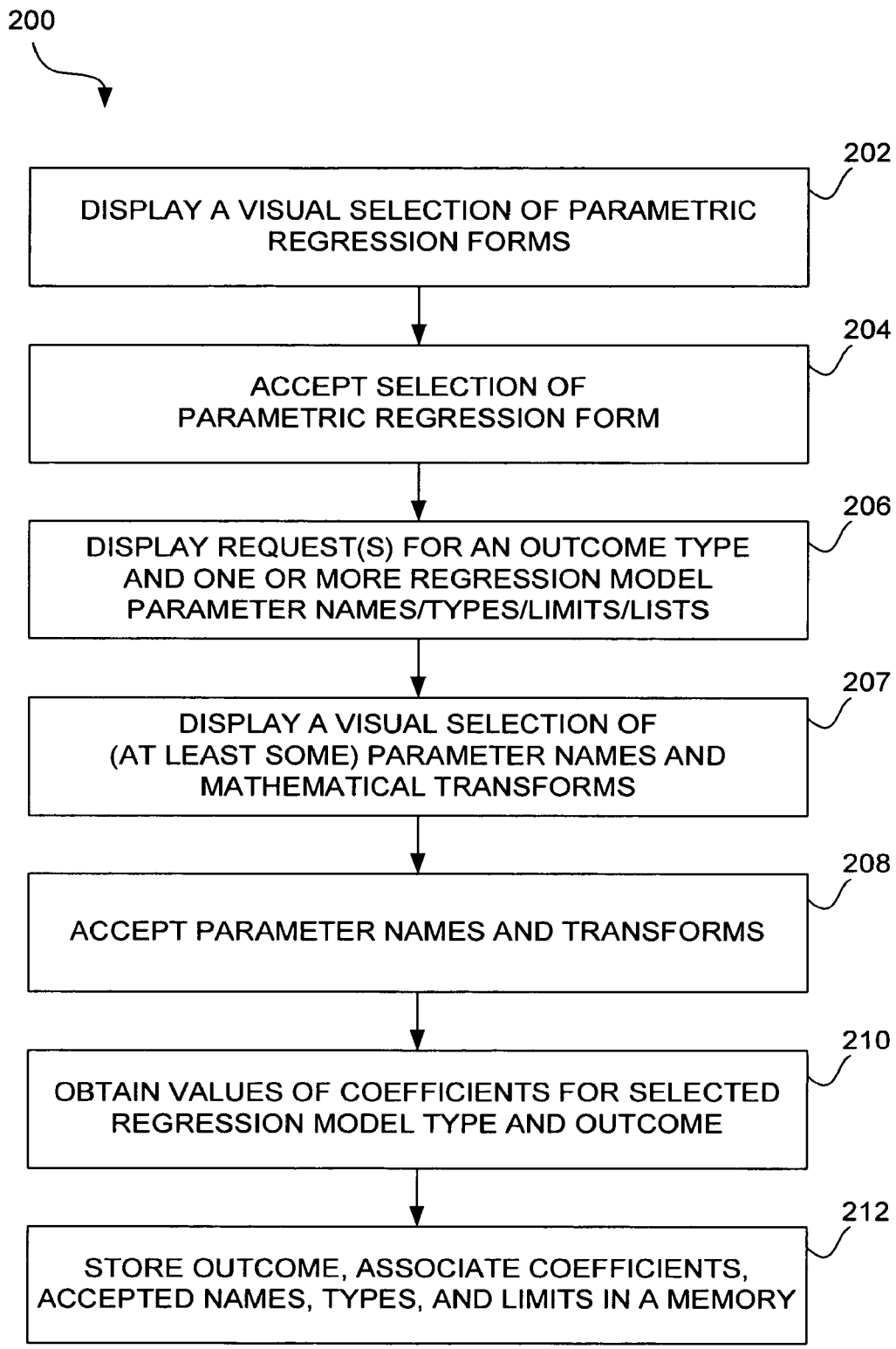
FIG. 3 is a flow chart illustrating instruction steps provided by some configurations of the server module of FIG. 2 in some configurations of the present invention.

More particularly, and referring to FIGS. 2 and 3, a server module 150 is provided on a machine readable medium or media. In some configurations of the present invention, server module 150 instructs processor 110 to perform a method illustrated by flow chart 200 of FIG. 2. Although the flow charts provided herein are illustrative of configurations of methods used herein, it will be understood that the order of steps shown can be varied from the order illustrated in other configurations of the present invention, that steps illustrated as being separate can be combined (e.g., various displays and requests for data can be combined into a single output screen), and that not all steps illustrated are necessarily required in all configurations.

A technical effect of the present invention is achieved first by a user logging in with appropriate credentials. Server module 150 instructs processor 110 to display, at 202, a visual selection of parametric regression model forms, for example, on a user display device 122. An example of such a display is shown in FIG. 4. In some configurations, access to these features is available only to those with administrative rights.

A Visual Model Editor (VME) is used in some configurations of the present invention to provide the visual selection of parametric regression model forms. A VME is a software application or module that provides a user with a graphical user interface (GUI) that allows the user to build, edit, and visualize statistical models. In some configurations, the GUI includes standard GUI elements such as windows, dialog boxes, menus, drop-down lists, radio-buttons, checkboxes, icons, etc; and the module provides functionality to define and express a statistical model using non-textual user input, such as mouse movements and mouse clicks. In some configurations, the module also provides functionality to input those parts of a model definition that require continuous (non-discrete) numeric values or free text (e.g., input parameter name or displayed text). User interaction with the interface is achieved by one or more methods that may include, for example, pointing and clicking with a mouse, touchpad, or other input device, or typing on a keyboard, or speaking into a microphone and using voice command recognition software. In some configurations, model definitions are imported, either in part in their entirety, from all-text model representations, examples of which include, but are not limited to, Predictive Modeling Markup Language (PMML) documents and other XML-based documents. Some configurations allow imported models to be edited and modified within the VME, stored in a memory of the server computer or elsewhere, and/or re-exported in their original formats and/or other formats.

A general regression model framework is used in some configurations for expressing predictions. The model types can include, for example, linear, generalized linear, cumulative multinomial, generalized multinomial and proportional hazard models, thereby providing coverage for major medical prognostic model types. For example, the selection may include a linear regression model of the form $f(x)=\beta_1 x_1 + \beta_2 x_2 + \beta_3 x_3 + \ldots + \beta_n x_n$ as well as intrinsically non-linear forms and forms that are linear in transformed variables, e.g., $x_1=\ln(y)$, where y is an input variable. Some configurations provide the ability to implement custom model types using a built-in scripting interface. The visual display of model type is associated with a drop-down list in some configurations, for example, and the visual display of model type changes depending upon the item selected from the drop-down list. In some configurations, the display is a list of parametric regression model forms. In other configurations, the display comprises a rendering of mathematical models on user display device 122.

Model types are defined in terms of a coefficient vector and an optional covariance matrix for calculating confidence intervals. For example, the coefficient vector and covariance matrix are defined as follows:

Coefficient vector $b'=(b'_0, b'_1, b' \ldots b'_r)$; and $$\text{Covariance matrix} \begin{bmatrix} v_{1\text{-}1} & v_{1\text{-}2} & \cdots & v_{1\text{-}r} \\ v_{2-1} & v_{2\text{-}2} & \cdots & v_{2\text{-}r} \\ \vdots & \vdots & & \vdots \\ v_{r\text{-}1} & v_{r\text{-}2} & \cdots & v_{r\text{-}r} \end{bmatrix} \text{ where}$$

$$v_{i \cong j \cong} == \text{Cov}(b_i, b_j) = \begin{bmatrix} v_{i1j1} & v_{i1j2} & \cdots & v_{i1js} \\ v_{i2-j1} & v_{i2j1} & \cdots & v_{i2js} \\ \vdots & \vdots & & \vdots \\ v_{isj1} & v_{isj2} & \cdots & v_{isjs} \end{bmatrix}$$

In the definitions above, $b_i = (b_{i1}, b_{i2} \ldots b_{is})$ is the vector of coefficients associated with the $i^{th}$ predicator in x, with one coefficient for each state s (except the reference state). Also, $v_{ikil} = \text{Cov}(b_{ik} b_{jl})$ denotes the covariance between the $i^{th}$ predictor, $k^{th}$ state) and $j^{th}$ predictor, $l^{th}$ state) coefficients.

The user at client computer 112 enters a selection of a model type (for example, a selection of one of the following model types: linear, generalized linear, cumulative multinomial, generalized, multimomial or proportional hazard model) from a menu. In some configurations, the menu is a "visual" menu. ("Visual" displays and menus include one or more elements such as graphical illustrations, drop-down lists, selection buttons, checklists, etc.) Server computer 102 is programmed with instructions by the server module to accept this selection at step 204. In some configurations, the actual form of mathematical model selected is determined by several user-selected options, all of which comprise the selection accepted by the server module at step 204. In such configurations, the user is, in effect, "building" the mathematical formulae as he or she goes along, as opposed to merely selected a static, pre-defined functional form.

Next, at step 206, instructions in the server module instruct processor 110 to request an outcome type and one or more regression model parameter names and corresponding parameter types, and, in appropriate cases, limits and/or lists of possible input values. Examples of parameter names in a medical or surgical environment could include one or more of, "blood pressure," "diabetes," "ejection fraction," and/or other statically significant parameters. In such an environment, one or more of these names and/or one or more other, different names might be supplied in response to this request. Examples of parameter types that may be supplied in response to a request include (not necessarily in correspondence to the example parameter names) "binary," "enumerated," "positive integer," "decimal", etc. An example of a possible limit is a range from 0 to 120, which might, for example, be a limiting range appropriate for an "Age" parameter name, and an example of a list of possible input values is "Male, Female" for a "Sex" parameter name. The parameter types and lists of possible input values can be used to select appropriate input formats when the model is used (e.g., a dropdown list for a parameter name having an associated list). The limits can be used to check the "sanity" of input values and to determine an appropriate corrective action when an inappropriate value is entered for a parameter, e.g., the value "250" for "Age."

In some configurations, the request for model parameters is sent via an XML Web Service for programmatic access. In configurations in which the request is sent via an XML Web Service, the request is not necessarily "displayed" as such. More specifically, a Remote Modeling Service is provided that uses a Web Method entitled "GetModelParameters" that takes, as its argument, a unique model identifier for the model of interest. The GetModelParameters method returns a listing, which may be a complete listing, of parameters required by that model. In some configurations, a GetParametersForRequestedModels accepts a plurality of unique model identifiers as its argument and returns a listing of parameters, without redundancy, of parameters required by those models. Also, in some configurations, the listing is returned together with type and/or validation information for some or all of the parameters required by the model. The entire request is communicated in some configurations over SOAP. Data collected corresponding to the parameters requested and in response to the request is returned to the server, in some configurations, via the XML web service. The returned data is then used for execution in the requested models, and results of the execution are returned to the requesting client over the XML web service.

In some configurations, the instructions for step 206 do instruct the outcome type request and the request for one or more regression model parameter names, etc., to be displayed. An example of an outcome type screen used in some configurations is shown in FIG. 5 and an example of a parameter name screen is shown in FIG. 6. At step 207, some configurations of the present invention also display a visual selection of at least some of the parameter names along with a visual selection of mathematical transforms for each displayed name. The user selects a transform, which can include, for example, logarithms, exponentials, squares, square roots, and other transformations, so that these functions of the values later used for each corresponding variable name are used in the regression equation instead of the variables themselves. In some configurations of the present invention, transformations are rendered on a display screen in a recognizable form, for example, a standard mathematical form. For example, in some configurations, if a power transformation is selected for a parameter, say, the square of "Age," the display for this transformation is rendered as "Age$^2$" wherever appropriate. In some configurations, scripting of transformations is made available for custom, unique, or complex transformations that are not otherwise provided for selection.

At step 208, these names, parameter types, parameter limits, and/or parameter transforms are accepted by processor 110. At step 210 (which may be combined with step 208), values of the coefficients (and/or other types of values, if needed by the model) for the selected regression model type and outcome are obtained. As used herein, the terms "coefficients" and "coefficient values," unless otherwise explicitly specified, are intended to include within their scope not only coefficients, but also any constant or other terms that may be necessary for a model. Such terms may include, for example, an intercept term, a mean square error term, and/or a number of degrees of freedom term. Thus, even though model forms are built from "standard components," in some configurations they may be considered as fluid forms rather than predefined static structures into which coefficient values are simply "dropped." For example, the number of terms used from a model form may itself be defined by defining the number of degrees of freedom term. In addition, "coefficient" data, as used herein, also includes, unless explicitly stated, data computed "on-the-fly" from one or more parent parameters (e.g., the data is computed as a function of another parameter that is retrieved from a database or requested as input). For example, some configurations allow the specification of or provide automatic recognition of at least some "parent-child" parameter relationships. For example, body mass index (BMI) can be defined as a constant times height divided by the square of the weight of a person. Thus, if one model uses BMI as a variable, and BMI is not available in a database but both height and weight are available, some configurations of the present invention will automatically calculate BMI from height and weight without issuing a separate request for BMI. If, in this example, a previous value of BMI exists for some reason and differs from the automatically calculated value, some configurations of the present invention display an alert icon next to the BMI parameter on the data input form.

In some configurations, the coefficient values are obtained by requesting that the values be input by a user at first client computer 112. In other configurations, these values are obtained by instructions to processor 110 to run a regression analysis on data obtained from a database 140, which may be a local database stored in computer 104 or a database accessible via a network such as network 113. A list comprising the outcome, associated coefficients and accepted names, types, and/or limits for variables are stored in a memory (e.g., memory 106, a secondary storage unit, or even a register of the processor) of server computer 106 for later use at step 212. (The term "later use" is intended to be interpreted broadly and can include, for example, use as part of the running of a stored model at a later date, use as part of a self-contained PDA version of the application, or use by a non-registered user who approached the application through the web to do a 'one-off' run of a model.) In some configurations in which a visual selection of mathematical variable transforms has been selected, an indication of the selected mathematical variable transforms and corresponding variable names is also stored in the memory. Some configurations also update β-weights and covariance matrices that are stored for the model.

In some configurations, derived parameters (for example, "Age Under 65," which is derived from "Age," or "BMI,"

which is derived from "Height" and "Weight") are stored, even though not explicitly collected from a user. The storing of "derived" regression model parameters and/or "derived" parameter names, unless otherwise explicitly stated, is considered consistent with and within the scope of "storing an accepted list of one or more regression model parameters and parameter names."

In some configurations, the procedure represented by flow chart 200 (or by variations thereof such as those described herein) represents the input of a regression model specification for (for example) a specific treatment and a specific outcome. The procedure represented by flow chart 200 (or its variations) can be repeated to add further regression model specifications representing different combinations of variables for different procedures, such as medical or surgical procedures. Some configurations further allow the editing and/or deletion of stored models. The parameters of regression model specifications are also referred to herein as variables and/or functions of variables, such as in regard to steps in which values to the variables or functions of variables are assigned.

Figure 7:
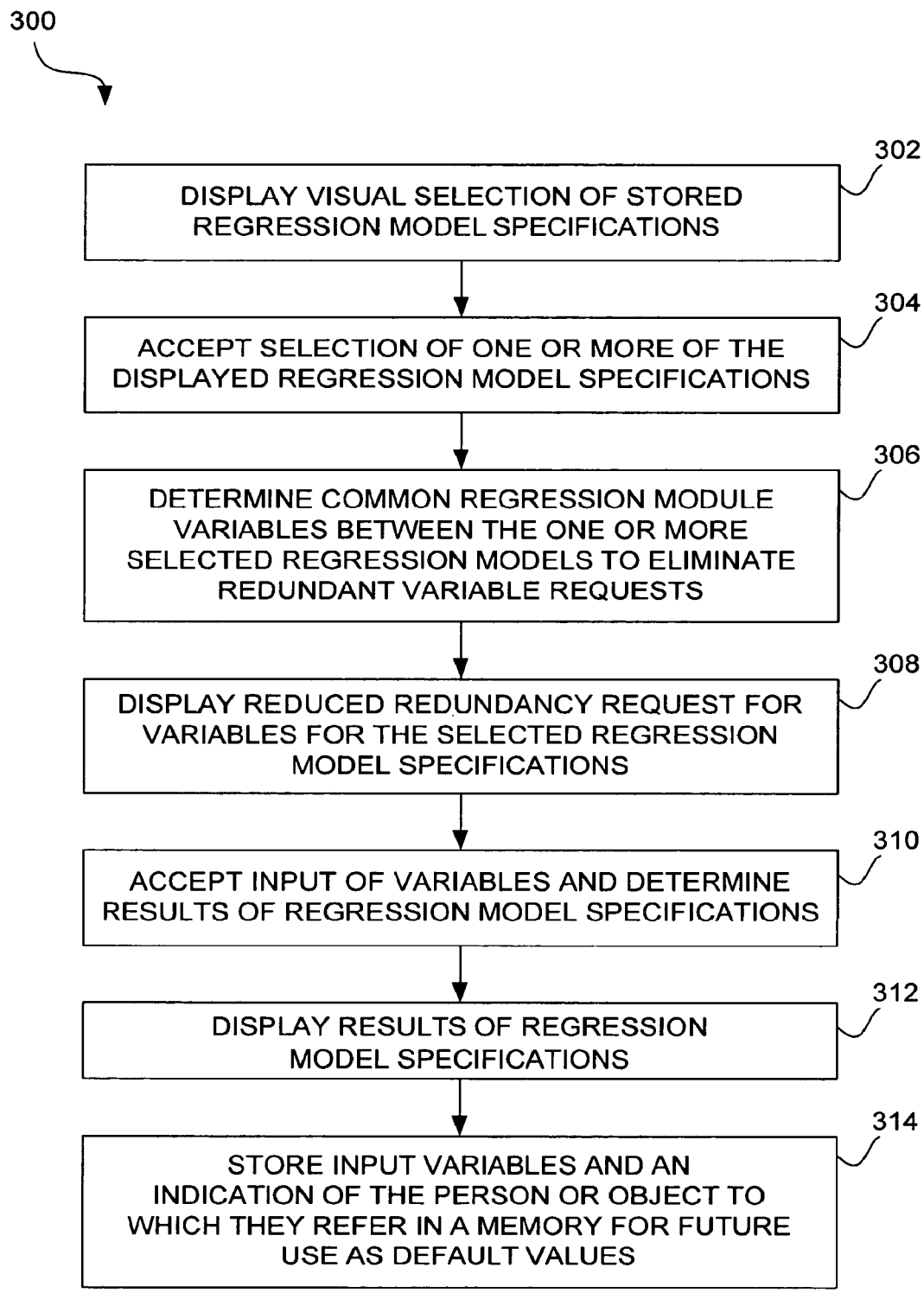
FIG. 7 is a flow chart illustrating additional instruction steps provided by some configurations of the server module of FIG. 2 in some configurations of the present invention.

Referring next to flow chart 300 of FIG. 7, server module 150 also contains instructions configured to instruct processor 110 to allow a user (usually, but not necessarily different from the user at first client computer 112) at second client computer 126 to log into the server module. The user at second client computer 126 is able to select one or more of the stored regression model specifications, input data for the stored models, run a regression analysis and be presented with results of the regression analysis or analyses. More particularly, at step 302, processor 110 is instructed to display a selection (for example, a visual selection) of previously stored regression model specifications on second user display device 136 by communicating data via network 113 with a program (e.g., a web browser) running on second client computer 126. An example of a display that provides a visual selection of previously stored regression model specifications is shown in FIG. 8. A user at second client computer 126 uses second user input device 138 to indicate a selection of one or more of the displayed regression model specifications, and this selection is communicated to processor 110 via network 113, and processor 110 is instructed to accept this selection at step 304. At step 306, the server module determines common regression module variables (for example, those corresponding to the same parameter name) between the one or more selected, stored regression models so that redundant requests for variables can be eliminated or reduced. The elimination of redundant requests for variables (i.e., requesting the same variable more than once when a plurality of stored regression model specifications is selected by the user) is also referred to herein as a "reduced-redundancy" request for variables. In some configurations, derived values from parent variables are also computed, so that data redundancy (not just model variable redundancy) is reduced or eliminated. For example, if one model requires "Age" as a continuous variable, and another model requires "Age less than 65" as a binary variable, some configurations of the present invention will not render the second parameter (i.e., "Age less than 65") for input, because it is redundant. Instead, these configurations automatically calculate the value of "Age less than 65" based upon the supplied "Age" value. (In this example, "Age less than 65" is input as a mathematical or other type of expression from which its dependence upon "Age" can be determined rather than as a separate, independent binary variable when the model is defined, so that its dependence upon the variable "Age" can be recognized.)

Figure 10:
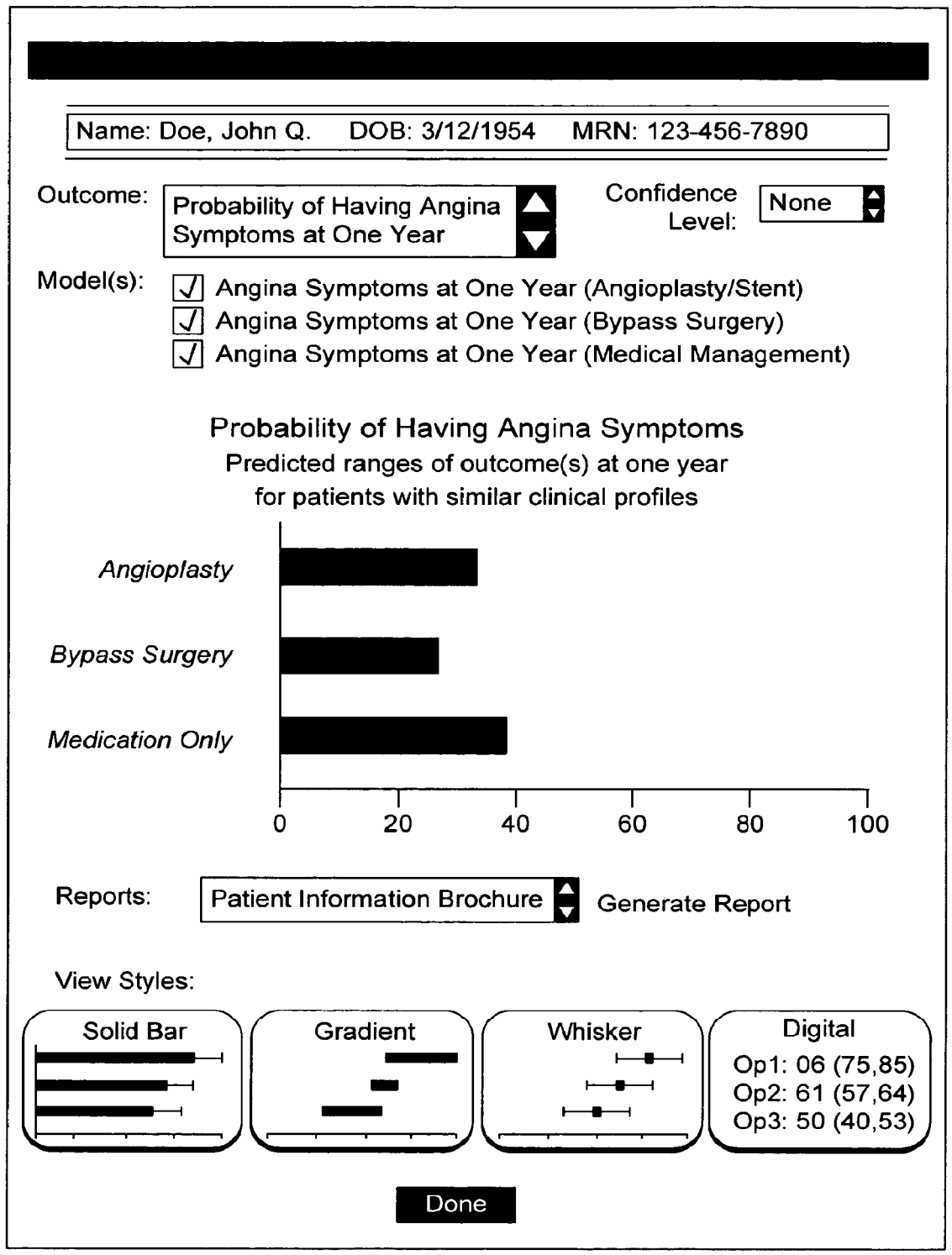
FIG. 10 is an example of a result display provided by some configurations of the present invention.

Thus, at step 308, the server module displays a request or requests for variables that correspond to the selected regression model specifications. An example of such a displayed request is shown in FIG. 9. The server module accepts the collected variable data at 310 (which may also include an identification of a person or object to which the variables apply) and runs the selected regression model specifications. At step 312, results of the selected regression model specifications are displayed. An example of such a display is shown in FIG. 10. The displayed results can also include a representation of a statistical range, such as a visual representation in some configurations. Also in some configurations, at step 314, processor 110 is instructed to use customizable content (for example, letterhead data), previously stored in a memory or database accessible to processor 110 and optionally including return addresses, logos, etc. to print the results or to cause the results to be printed. (Customizable content is not limited to letterhead, need not include the letterhead, and can include, in various configurations, all or any portion or portions of the entire report. By way of non-limiting example, the report can be customized in some configurations to be "informed consent" or similar type of document. An "informed consent" document can, in some configurations, include customization to provide applicable terms under which treatment is provided, disclaimers, and/or signature lines for patients and/or another person or persons authorized to provide consent for treatment. Other types of reports can include signature lines for a patient or his representative or guardian to sign confirming, for example, that the risks involved in undergoing or not undergoing a certain course of treatment have been explained and understood.) The server module can include instructions to print different letterheads (or other types of documents) depending upon credentials (e.g., login information) provided by the current user. Also, in some configurations, instructions to processor 110 at step 316 cause processor 110 to store variables apply in a memory or database (such as memory 104) accessible to processor 110. Instructions in the server module are provided to instruct processor 110 to provide default values for the stored variables when outcome results of the same or different type are requested for that person or object at a different time.

More particularly in some configurations, at runtime, collected model parameters (i.e., user inputs) are serialized into a Predictor Vector:

$$x' = (x_1 \ x_2 \ \ldots \ x_r) = \begin{cases} (1 \ z') & \text{Intercept} \\ z' & \text{No Intercept} \end{cases}$$

where z is the transformed response vector, each of whose elements correspond to a single data item (e.g., systolic blood pressure).

The Linear Predictor is then calculated as $$\hat{\eta}' = (\hat{\eta}_{1,2} \ldots \hat{\eta}_s) = (x'(e_1 \cdot b) x'(e_2 \cdot b) \ldots x'(e_s \cdot b))$$

in which each $e_i$ is an extraction vector derived from the appropriate Extraction Matrix:

$$E = \begin{pmatrix} e'_1 \\ e'_2 \\ \vdots \\ e'_s \end{pmatrix} \quad\quad\quad \text{I}$$

where each row $e_i'$ identifies the relevant sub-vector of b and the sub-matrix of V needed to predict the $i^{th}$ independent parameter of the predictand. The extract form of E is dependent on the model type (see Table 1).

TABLE 1

Extraction Matrices

| Model Type | Intercept | No Intercept |
|---|---|---|
| Linear | $1_{1\times(r+1)}$ | $1_{1\times r}$ |
| Generalized Linear | $1_{1\times(r+1)}$ | $1_{1\times r}$ |
| Cumulative Multinomial | $[I_{s\times s}\ 1_{s\times r}]$ | $[I_{(s-1)\times(s-1)}\ 1_{(s-1)\times r}]$ |
| Generalized Multinomial | $\begin{bmatrix} I_{s\times s} \cdots I_{s\times s} \\ r+1 \text{ times} \end{bmatrix}$ | $\begin{bmatrix} I_{s\times s} \cdots I_{s\times s} \\ r \text{ times} \end{bmatrix}$ |
| Proportional Hazards | N/A | $1_{1\times r}$ |

In the table above, I denotes the identity matrix (i.e., a matrix with all diagonal entries=1 and all off-diagonal entries=0), and 1 denotes a matrix of all 1s.

The Prediction Vector containing the outcome point-estimate(s) is then given by $$\hat{\mu} = g^{-1}(\hat{\eta})$$

where $g^{-1}$ is the appropriate inverse link function (see Table 2). The Linear Predictor Variance Vector is given by $$\hat{\sigma}'^2 = (x'(e_1 \cdot v)x\ x'(e_2 \cdot v)x \ldots x'(e_s \cdot v)_x)$$

from which confidence intervals can be calculated as $$(\hat{\mu}_{LO}, \hat{\mu}_{HI}) = g^{-1}(\hat{\eta} \pm F_v^{-1}(1-\alpha/2)\sqrt{\hat{\phi}^2 + \hat{\rho}^2})$$

where $F_v^{-1}$ is the inverse t-distribution function with v degrees of freedom at confidence level $\alpha$ and $\hat{\phi}^2$ is the mean square error ($\hat{\phi}^2$ defined only for linear models).

TABLE 2

Inverse Link Functions

| | |
|---|---|
| Identity | $\mu = \eta$ |
| Log | $\mu = e^\eta$ |
| Logit | $\mu = (1 + e^{-\eta})^{-1}$ |
| Probit | $\mu = \Phi(\eta)$ |
| Power | $\mu = \begin{cases} \eta^{1/\lambda} & \text{if } \lambda > 0 \\ e^\eta & \text{if } \lambda = 0 \end{cases}$ |
| Complementary log-log | $\mu = 1 - e^{-e^\eta}$ |
| Cumulative logit$^\tau$ | $\pi_i = (1 + e^{\eta - i})^{-1}\ i = 1, \ldots, s$ |
| Cumulative probit$^\tau$ | $\pi_i = \Phi(\eta_i)^*\ i = 1, \ldots, s$ |
| Cumulative complementary log-log$^\tau$ | $\pi_i = 1 - e^{-e^{\eta_i}}\ i = 1, \ldots, s$ |
| Generalized Logit | $\mu_i = \begin{cases} e^{\eta_i}\left(1 + \sum_{j=1}^s e^{\eta_j}\right)^{-1} & i = 1, \ldots, s \\ \left(1 + \sum_{j=1}^s e^{\eta_j}\right)^{-1} & i = s+1 \end{cases}$ |
| Proportional Hazards | $\mu = S_j^{e^\eta}$ |
| $^\tau$For multi-state models, | $\mu_i = \begin{cases} \pi_i & i = 1 \\ \pi_i - \sum_{j=1}^{i-1} \pi_j & i = 2, \ldots, s \\ 1 = \sum_{j=1}^{i-1} \pi_j & i = s+1 \end{cases}$ |

*$\Phi$ is the standard normal distribution function

In various configurations of the present invention, model building is greatly facilitated by a visual editing environment that provides dynamic on-screen instructions and rendering of prediction formulae as well as robust validation services. Parameters are identified that are used in a prediction formula. New parameters can be created de novo or selected from an existing parameter library (thereby allowing for standardization of parameter definitions across all models).

Once parameters have been defined, one or more data transformations can be assigned to each. A broad array of built-in transformation types are available to the user, and custom transformation types can be readily defined via scripting, allowing configurations of the present invention to handle a wide range of complex formulae.

Main effects and interaction terms derived from the input parameters and their transformations can be derived in some configurations of the present invention, and regression coefficients for calculating point estimates for outcome of interest and optional covariance estimates can be provided for computing confidence intervals.

Once regression model specifications have been built and deployed, health care providers (or, in other environments, other individuals) can readily access them through an integrated and customizable portal interface using a variety of web-enabled devices. Dynamically generated data entry screens are provided based on the variables required by the selected model(s). For example, in medical environments, data for patients can either be entered de novo or retrieved from a patient information system, which can be readily integrated with existing clinical information systems via XML web services support.

Some configurations of the present invention render model outputs in a variety of graphical and non-graphical formats, including solid bar plots, gradient bar plots, whisker line plots, pie charts, and/or digital LED-style displays, which can be user-selectable. Output from multiple models can be grouped onto a single plot to facilitate inter-model comparisons (for example, stroke risk with angioplasty versus bypass surgery). In addition, some configurations allow a user to customize the output plot style, the selection of models to include in a final output and the display of confidence intervals (when model covariance data has been provided). In various configurations, users can print outcome plots using customizable report templates in order to generate documents such as patient educational materials and informed consent sheets. Also in some configurations, outcomes researchers can customize report and page content using a built-in Microsoft Word®-like interface or by editing HTML code. A feature rich set of portal content modules, including workgroup directories, discussion threads, and document repositories can be provided in server module configurations of the present invention to allow outcomes research groups to easily create, manage, and build their own collaborative web sites.

It will thus be appreciated that configurations of the present invention can be used to handle various aspects of data collection, validation, storage/retrieval, and processing, thereby freeing outcomes researchers from intricacies of programming and networking.

While the invention has been described in terms of various specific embodiments, those skilled in the art will recognize that the invention can be practiced with modification within the spirit and scope of the claims.

What is claimed is:

1. A method for generating interfaces configured to receive patient variable data to be processed by mathematical health outcome prediction models, the method comprising:

receiving, by a computer system, an identification of a first plurality of mathematical health outcome prediction models;

accessing the first plurality of mathematical health outcome prediction models;

dynamically generating, by the computer system, an interface based at least in part on respective definitions of the first plurality of mathematical health outcome prediction models, wherein the dynamically generated interface is configured to request patient information corresponding to patient variables of the first plurality of mathematical health outcome prediction models, wherein the dynamically generated interface is configured by the computer system to reduce redundancy in the requested information at least in part by identifying one or more variables that may be shared among the first plurality of mathematical health outcome prediction models based at least in part upon the respective definitions of the first plurality of mathematical health outcome prediction models.

2. The method as defined in claim 1, wherein the interface retrieves patient information from a patient information system.

3. The method as defined in claim 1, wherein the interface obtains patient information from a patient information system using an XML web service without displaying the request.

4. The method as defined in claim 1, wherein the interface is provided for display to a user, and patient information entered by the user is received at the computer system.

5. The method as defined in claim 1, wherein the interface is configured to obtain patient information related to a patient's gender, age, and history of diabetes.

6. The method as defined in claim 1, the method further comprising providing a user interface for inputting a plurality of regression model specifications related to medical treatment and outcome.

7. The method as defined in claim 1, the method further comprising:
 (a) inputting a regression model specification related to providing health related predictions; and
 (b) repeating (a) a plurality of times to obtain and store a plurality of the regression model specifications.

8. The method as defined in claim 1, the method further comprising:
 (a) inputting a regression model specification related to providing health related predictions;
 (b) repeating (a) a plurality of times to obtain and store a plurality of the regression model specifications; and
 using results of the plurality of regression model specifications to create an informed consent document and/or patient educational material including a discussion of treatment risks and benefits.

9. The method as defined in claim 1, the method further comprising:
 (a) inputting a regression model specification related to providing health related predictions;
 (b) repeating (a) a plurality of times to obtain and store a plurality of the regression model specifications; and
 using results of the plurality of regression model specifications to create a clinical decision aid.

10. The method as defined in claim 1, the method further comprising:
 (a) inputting a health outcome prediction model specification related to providing health related predictions;
 (b) repeating (a) a plurality of times to obtain and store a plurality of health outcome prediction model specifications related to providing health related predictions;
 executing the plurality of health outcome prediction model specifications, the plurality of health outcome prediction model specifications corresponding to the first plurality of mathematical health outcome prediction models; and
 providing for display results of execution of the health outcome prediction model specifications.

11. The method as defined in claim 1, the method further comprising:
 (a) obtaining a health outcome prediction model specification related to providing health related predictions;
 (b) repeating (a) a plurality of times to obtain and store a plurality of health outcome prediction model specifications related to providing health related predictions;
 executing the plurality of health outcome prediction model specifications, the plurality of health outcome prediction model specifications corresponding to the first plurality of mathematical health outcome prediction models; and
 providing for display results of the execution of the plurality health outcome prediction model specifications.

12. A computer system configured to facilitate the use of health outcome prediction models, the computer system comprising:
 at least one computing device;
 memory coupled to the at least one computing device, the memory having instructions stored therein that when executed by the at least one computing device are configured to cause the computer system to perform operations comprising:
  receiving an identification of a first plurality of mathematical health outcome prediction models;
  accessing the first plurality of mathematical health outcome prediction models;
  dynamically generating an interface based at least in part on respective definitions of the first plurality of mathematical health outcome prediction models,
  wherein the dynamically generated interface is configured to request patient information corresponding to patient variables of the first plurality of mathematical health outcome prediction models,
  wherein the dynamically generated interface is configured to reduce redundancy in the requested information at least in part by identifying one or more variables that may be shared among the first plurality of mathematical health outcome prediction models based at least in part upon the respective definitions of the first plurality of mathematical health outcome prediction models.

13. The computer system as defined in claim 12, wherein the interface is configured to analyze patient information from a patient information system.

14. The computer system as defined in claim 12, wherein the interface is configured to obtain patient information from a patient information system using an XML web service without displaying the request.

15. The computer system as defined in claim 12, the operations further comprising providing the interface for display to a user, and receiving patient information entered by the user via the interface.

16. The computer system as defined in claim 12, wherein the interface is configured to obtain patient information related to a patient's gender, age, and history of diabetes.

17. The computer system as defined in claim 12, the operations further comprising providing a user interface for inputting a plurality of regression model specifications related to medical treatment and outcome.

18. The computer system as defined in claim 12, the operations further comprising:
    (a) inputting a regression model specification related to providing health related predictions; and
    (b) repeating (a) a plurality of times to obtain and store a plurality of the regression model specifications.

19. The computer system as defined in claim 12, the operations further comprising:
    (a) inputting a regression model specification related to providing health related predictions;
    (b) repeating (a) a plurality of times to obtain and store a plurality of the regression model specifications; and
    using results of the plurality of regression model specifications to create an informed consent document and/or patient educational material including a discussion of treatment risks and benefits.

20. The computer system as defined in claim 12, the operations further comprising:
    (a) inputting a health outcome prediction model specification related to providing health related predictions;
    (b) repeating (a) a plurality of times to obtain and store a plurality of health outcome prediction model specifications related to providing health related predictions;
    executing the plurality of health outcome prediction model specifications, the plurality of health outcome prediction model specification corresponding to the first plurality of mathematical health outcome prediction models; and
    providing for display results of execution of the plurality health outcome prediction model specifications.

21. The computer system as defined in claim 12, the operations further comprising:
    (a) obtaining a health outcome prediction model specification related to providing health related predictions;
    (b) repeating (a) a plurality of times to obtain and store a plurality of health outcome prediction model specifications related to providing health related predictions;
    executing the plurality of health outcome prediction model specifications, the plurality of health outcome prediction model specification corresponding to the first plurality of mathematical health outcome prediction models; and
    providing for display results of the execution of the plurality health outcome prediction model specifications.

22. The computer system as defined in claim 12, further comprising a server including a network interface configured to receive at least a portion of the patient variables from one or more client systems.

23. A non-transitory computer readable storage medium having instructions stored thereon that, if executed by a computing system, cause the computing system to perform operations comprising:
    receiving an identification of a first plurality of mathematical health outcome prediction models;
    accessing the first plurality of mathematical health outcome prediction models;
    dynamically generating an interface based at least in part on respective definitions of the first plurality of mathematical health outcome prediction models,
    wherein the dynamically generated interface is configured to request patient information corresponding to patient variables of the first plurality of mathematical health outcome prediction models,
    wherein the dynamically generated interface is configured to reduce redundancy in the requested information at least in part by identifying one or more variables that may be shared among the first plurality of mathematical health outcome prediction models based at least in part upon the respective definitions of the first plurality of mathematical health outcome prediction models.

24. The non-transitory computer readable storage medium as defined in claim 23, wherein the interface is configured to retrieve patient information from a patient information system.

25. The non-transitory computer readable storage medium as defined in claim 23, wherein the interface is configured to obtain patient information from a patient information system using an XML web service without displaying the request.

26. The non-transitory computer readable storage medium as defined in claim 23, the operations further comprising providing the interface for display to a user, and receiving patient information entered by the user via the interface.

27. The non-transitory computer readable storage medium as defined in claim 23, wherein the interface is configured to obtain patient information related to a patient's gender, age, and history of diabetes.

28. The non-transitory computer readable storage medium as defined in claim 23, the operations further comprising providing a user interface for inputting a plurality of regression model specifications related to medical treatment or condition and outcome.

29. The non-transitory computer readable storage medium as defined in claim 23, the operations further comprising:
    (a) inputting a regression model specification related to providing health related predictions; and
    (b) repeating (a) a plurality of times to obtain and store a plurality of the regression model specifications.

30. The non-transitory computer readable storage medium as defined in claim 23, the operations further comprising:
    (a) inputting a regression model specification related to providing health related predictions;
    (b) repeating (a) a plurality of times to obtain and store a plurality of the regression model specifications; and
    using results of the plurality of regression model specifications to create an informed consent document and/or patient educational material including a discussion of treatment risks and benefits.

31. The non-transitory computer readable storage medium as defined in claim 23, the operations further comprising:
    (a) inputting a health outcome prediction model specification related to providing health related predictions;
    (b) repeating (a) a plurality of times to obtain and store a plurality of health outcome prediction model specifications related to providing health related predictions;
    executing the plurality of health outcome prediction model specifications, the plurality of health outcome prediction model specification corresponding to the first plurality of mathematical health outcome prediction models; and
    providing for display results of the execution of the plurality health outcome prediction model specifications.

32. The non-transitory computer readable storage medium as defined in claim 23, the operations further comprising:
    (a) obtaining a health outcome prediction model specification related to providing health related predictions;
    (b) repeating (a) a plurality of times to obtain and store a plurality of health outcome prediction model specifications related to providing health related predictions;
    executing the plurality of health outcome prediction model specifications, the plurality of health outcome prediction model specifications corresponding to the first plurality of mathematical health outcome prediction models; and
    providing for display results of execution of the health outcome prediction model specifications.

* * * * *

UNITED STATES PATENT AND TRADEMARK OFFICE
CERTIFICATE OF CORRECTION

PATENT NO. : 8,560,281 B2
APPLICATION NO. : 13/615401
DATED : October 15, 2013
INVENTOR(S) : Soto et al.

It is certified that error appears in the above-identified patent and that said Letters Patent is hereby corrected as shown below:

Title Page, References Cited, in column 2 (page 2, item 56) at line 30, Under Other Publications, change "result" to --results--.

In the Specification

In column 4 line 34, change "and./or" to --and/or--.

In column 6 line 59, change "multimomial" to --multinomial--.

In column 10 line 56, change " $\hat{\eta}=(\hat{\eta}_{1,2}\ldots\hat{\eta}_s)=(x'(e_1,b)x'(e_2,b)\ldots x'(e_s,b))$ " to -- $\hat{\eta}=(\hat{\eta}_1\,\hat{\eta}_2\ldots\hat{\eta}_s)=(x'(e_1\cdot b)\;x'(e_2\cdot b)\;\cdots x'(e_s\cdot b))$ --.

In column 11 line 13, change "Mulitnomia 1" to --Multinomial--.

In column 11 line 14, change "Multinomia 1" to --Multinomial--.

In the Claims

In column 14 line 8, In Claim 10, change "of execution of the health" to --of the execution of the plurality health--.

In column 15 line 27, In Claim 20, change "specification" to --specifications--.

In column 15 line 29, In Claim 20, change "of execution" to --of the execution--.

In column 15 line 39, In Claim 21, change "specification" to --specifications--.

In column 16 line 47, In Claim 31, change "specification" to --specifications--.

In column 16 line 62, In Claim 32, change "of execution of the health" to --of the execution of the plurality health--.

Signed and Sealed this
Twentieth Day of May, 2014

Michelle K. Lee
*Deputy Director of the United States Patent and Trademark Office*